(12) United States Patent
Morse et al.

(10) Patent No.: US 7,831,451 B1
(45) Date of Patent: Nov. 9, 2010

(54) SYSTEMS AND METHODS FOR INSURANCE UNDERWRITING

(75) Inventors: Robert D. Morse, Cota de Caza, CA (US); Gerald L. Conrad, Cota de Caza, CA (US); Linda Goodwin, Concord, NC (US); Loren S. Kane, Matthews, NC (US); Harry W. Clark, Ridgefield, CT (US)

(73) Assignee: Quantitative Data Solutions, Inc., Rosemont, IL (US)

( * ) Notice: Subject to any disclaimer, the term of this patent is extended or adjusted under 35 U.S.C. 154(b) by 1755 days.

(21) Appl. No.: 10/875,798

(22) Filed: Jun. 25, 2004
(Under 37 CFR 1.47)

Related U.S. Application Data

(60) Provisional application No. 60/482,761, filed on Jun. 27, 2003.

(51) Int. Cl.
*G06Q 40/00* (2006.01)
(52) U.S. Cl. .................................. 705/4; 705/3; 705/2
(58) Field of Classification Search ........................ None
See application file for complete search history.

(56) References Cited

U.S. PATENT DOCUMENTS

| | | | |
|---|---|---|---|
| 4,975,840 A | 12/1990 | DeTore et al. | |
| 5,732,397 A | 3/1998 | DeTore et al. | |
| 5,873,066 A * | 2/1999 | Underwood et al. | 705/4 |
| 7,319,970 B1 * | 1/2008 | Simone | 705/4 |
| 7,698,155 B1 * | 4/2010 | Prasad et al. | 705/3 |
| 7,698,158 B1 * | 4/2010 | Flagg | 705/4 |
| 2001/0053986 A1 * | 12/2001 | Dick | 705/3 |
| 2002/0087364 A1 * | 7/2002 | Lerner et al. | 705/4 |
| 2002/0111833 A1 * | 8/2002 | Dick | 705/3 |
| 2002/0111835 A1 | 8/2002 | Hele et al. | |
| 2002/0188476 A1 | 12/2002 | Bienvenu, II et al. | |
| 2003/0009355 A1 * | 1/2003 | Gupta | 705/2 |

(Continued)

OTHER PUBLICATIONS

Adopt a Proactive Approach; Greg Linde; Best's Review Life/Health Edition , v 99 , n 10 , p. 67; Feb. 1999; 2 pages.*

(Continued)

*Primary Examiner*—Hani Kazimi
*Assistant Examiner*—Gregory Johnson
(74) *Attorney, Agent, or Firm*—Pillsbury Winthrop Shaw Pittman LLP

(57) ABSTRACT

Embodiments of the present invention relate to systems and methods for automating insurance underwriting by integrating information from multiple online databases and creating decision making advice useful to insurance underwriters. One system includes a client, database, and server. The client allows an underwriter to enter applicant information, enter customized risk modifiers, and receive an underwriting decision. The database provides additional applicant information. This information can include one or more of prescription drug history, credit history, motor vehicle records, and geocentric mortality risk. The server obtains the applicant information, calculates the applicant's risk, makes an underwriting decision. Another system calculates a prescription drug risk for an applicant from pharmacy benefits management data, drug risk category data, and application data. Another system calculates a geocentric mortality risk for an applicant from census data, mortality data, credit information, and application data. Preset external modifiers are added to systems and methods of calculating risk in order to allow the underwriter to customize the risk results.

23 Claims, 8 Drawing Sheets

U.S. PATENT DOCUMENTS

| | | | | |
|---|---|---|---|---|
| 2003/0233260 A1* | 12/2003 | Snell et al. | | 705/4 |
| 2004/0039600 A1* | 2/2004 | Kramer et al. | | 705/2 |
| 2006/0218023 A1 | 9/2006 | Conrad | | 705/4 |

OTHER PUBLICATIONS

New LTC Underwriting Tools On The Way; Tedd C. Determan; National Underwriter Life & Health-Financial Services Edition , v 104 , n 33 , p. 22; Aug. 14, 2000, 2 pages.*

Life Insurers Can Regain Mass Market, Thomson Writes in Best's Review; New Technology Streamlines Underwriting and Issuance; Business Wire, p. 2037; Jun. 5, 2002 2 pages.*

Prescription Drug History May Speed Underwriting Process; National Underwriter Life & Health-Financial Services Edition , v 105 , n 28 , p. 32; Jul. 9, 2001; 2 pages.*

Ron Panko, "Common Denominators"; Best's Review; Sep. 2002; pp. 95-96, 98 & 100.

Consumer Quote USA; "Underwriting Explained" , Jun. 2003; 2 pages.

Insurance.com; "Term Insurance Underwriting"; Jun. 2003; 3 pages.

Gen Re™ Life Health, "At Your Service—Life and Disability Underwriting Software", Kölnische Rückversicherungs-Gesellschaft AG, 2003, <http://www.genre.com/sharedfile/pdf/CompassCLUE-en.pdf>, pp. 1-16.

Transamerica Reinsurance, "Impact of New CSO Tables on Term Insurance Varies", *The Messenger; Transamerica Reinsurance Risk Management Newsletter,* Third Quarter 2001, vol. 3, Issue 3, USA, <http://www.transamericareinsurance.com/Files/Messenger_3rd_quarter2001.pdf>, pp. 1-8.

CA™ Industry Solutions, "Reducing Costs and Automating Agent/Sales Processes", CA Industry Solutions Website, © 2006, <http://www3.ca.com/technologies/subsolution.aspx?id=4801>.

Mark Franzen, FSA, Ph.D., IntelRx, "New Approaches in Underwriting Using Prescription Drugs", Jun. 24, 2002, USA, http://handouts.soa.org/conted/cearchive/sanfran02/026_franzen.pdf, pp. 1-8.

Society of Actuaries, "Session 99PD, Using Prescription Drug Data for Risk Adjustment and Underwriting/Rating", *Record,* vol. 27, No. 3, New Orleans Annual Meeting, Oct. 21-24, 2001, USA, http://library.soa.org/library/record/2000-09/RSA01V27N399PD.pdf, pp. 1-22.

Louise H. Anderson, James A. Minnich, Ingenix, Inc., "Small Group Renewal Underwriting Using the Ingenix Predictive Model", © 2001 Ingenix, Inc., USA, www.reden-anders.com/pdf/PredictiveModelingWhitePaper.pdf, pp. 1-12.

Mark Merlis, "Fundamentals of Underwriting in the Nongroup Health Insurance Market: Access to Coverage and Options for Reform", *National Health Policy Forum, NHPF Background Paper,* Apr. 13, 2005, Washington, D.C., http://www.nhpf.org/pdfs_bp/BP_Underwriting_04-13-05.pdf, pp. 1-29.

LabOne, ScriptCheck Update, "The Latest News", vol. 2, Dec. 23, 2004, USA, http://www.labone.com/enews/enews1204.html#scriptcheck, 5 pages.

David Dorans, "Outsourcing as a Competitive Advantage", *The Messenger; Transamerica Reinsurance Risk Management Newsletter,* Dec. 2005, USA, <http://www.transamericareinsurance.com/Files/Messenger_4q05.pdf>, 8 pages.

Milliman Consultants and Actuaries, "Individual Medical Underwriting Guidelines", USA, http://www.milliman.com/tools_products/medical_underwriting_guidelines.IMUG.pdf, pp. 1-6.

Gen Re Life Health; At Your Service—Life and Disability Underwriting Software; pp. 1-16; Kolnische Ruckversicherungs—Gessellshaft AG 2003; http://www.genre.com/sharedfile/pdf/CompassCLUE-en.pdf.

Transamerica Reinsurance; Impact of New CSO Tables on Term Insurance Varies; The Messenger, Transamerica Reinsurance Risk Management Newsletter; pp. 1-8; Third Quarter 2001, vol. 3, Issue 3; USA; http://www.transamericareinsurance.com/Files/Messenger_3rd_quarter2001.pdf.

CA Industry Solutions; Reducing Costs and Automating Agent/Sales Processes; CA Industry Solutions Website; CA 2006; http://www3.ca.com/technologies/subsolution.aspx?id=4801.

Mark Franzen, FSA, Ph.D., IntelRx; New Approaches in Underwriting Using Prescription Drugs; Jun. 24, 2002; pp. 1-8; USA; http://handouts.soa.org/conted/cearchive/sanfran02/026_franzen.pdf.

Society of Actuaries; Session 99PD; Using Prescription Drug Data for Risk Adjustment and Underwriting/Rating; Record, vol. 2 7, No. 3; New Orleans Annual Meeting Oct. 21-24, 2001; pp. 1-22; USA; http://library.soa.org/library/record/2000-09/RSA01V27N399PD.PDF.

Louise H. Anderson, James A. Minnich, Ingenix, Inc.; Small Group Renewal Underwriting Using the Ingenix Predictive Model; 2001 Ingenix, Inc.; pp. 1-12; USA; www.reden-anders.com/pdf/PredictiveModelingWhitePaper.pdf.

Mark Merlis; Fundamentals of Underwriting in the Nongroup Health Insurance Market: Access to Coverage and Options for Reform; National Health Policy Forum; NHPF Background Paper; Apr. 13, 2005; pp. 1-29; Washington D.C.; http://www.nhpf.org/pdfs_bp/BP_Underwriting_04-13-05.pdf.

Labone; ScriptCheck Update; The Latest News vol. 2; Dec. 23, 2004; USA; http://www.labone.com/enews/enews1204.html#scriptcheck.

David Dorans; Outsourcing as a Competitive Advantage; The Messenger, Transamerica Reinsurance Risk Management Newsletter; Dec. 2005; USA; http://www.transamericareinsurance.com/Files/Messenger_4q05.pdf.

Milliman USA Consultants and Actuaries; Individual Medical Underwriting Guidelines; pp. 1-6; USA; http://www.milliman.com/tools_products/medical_underwriting_guidelines/IMUG.pdf.

* cited by examiner

SYSTEMS AND METHODS FOR INSURANCE UNDERWRITING

CROSS-REFERENCE TO RELATED APPLICATION

This application claims the benefit of U.S. Provisional Patent Application Ser. No. 60/482,761, filed Jun. 27, 2003, which is incorporated herein by reference.

BACKGROUND OF THE INVENTION

1. Field of the Invention

Embodiments of the present invention relate to systems and methods for insurance underwriting. More particularly, embodiments of the present invention relate to systems and methods that integrate information from multiple online databases and create decision making advice useful to insurance underwriters.

2. Background Information

Underwriting is the process an insurance company uses to determine whether or not a potential customer is eligible for insurance, and the rate that that potential customer should pay for the insurance if eligible. The purpose of insurance underwriting is to spread risk among a pool of insured in a manner that is both fair to the customer and profitable for the insurer. Like other businesses, insurance companies need to make a profit. Therefore, it does not make sense for them to sell term insurance, for example, to everyone who applies for it. Although they do not want to make customers pay an excessively high rate, it is not wise for them to charge all their policyholders the same premium. Underwriting enables the company to "weed out" certain applicants and to charge the remaining applicants premiums that are commensurate with their level of risk.

Risk classification determines to a significant degree the premium a customer will pay for insurance. Four typical risk groups are: standard, preferred, substandard, and uninsurable. Each of these is explained below.

Standard risks: These are individuals who, according to the insurance company's underwriting standards, are entitled to term insurance without having to pay a rating surcharge or be subjected to policy restrictions.

Preferred risks: This group includes individuals whose mortality experience (i.e., life expectancy) as a group is expected to be above average and to whom the company offers a lower than standard rate. The most common preferred class today is nonsmokers, for whom many insurers now offer a favorable rate.

Substandard risks: These are individuals who, because of their health and/or other factors, cannot be expected (on average) to live as long as people who are not subject to these risk factors. Substandard applicants are insurable, but only at higher than standard rates that reflect the added risk. Policies issued to substandard applicants are referred to as rated or extra risk policies.

Uninsurable: These are applicants to whom the company refuses to sell term insurance because they are unwilling to shoulder the risks. They have decided that the risk factors associated with the applicant are too great or too numerous. In other cases, the applicant's circumstances may be so rare or unique that the company has no basis to arrive at a suitable premium.

An insurance company typically looks at a number of factors during the underwriting process in order to evaluate a potential customer in terms of risk. These factors enable the insurer to decide whether or not the potential customer is insurable. If the potential customer is insurable, these factors help place them into the appropriate risk group. Some of the factors considered are age, sex, current health/physical condition, personal health history, family health history, financial condition, personal habits/character, occupation, and hobbies.

An insurance company will gather information about potential customers from several sources. In the case of term insurance, the basic source of underwriting information is a completed customer application. The questions on the application are designed to give the insurer much of the information needed to make a decision. The company will then either reject an application, accept it and offer insurance at a certain rate, or seek additional information. In many cases, the company places great weight on the recommendations of a broker or insurance agent, particularly if the broker or agent has a good track record with the company. In some cases, an insurer may request a report from an independent company that specializes in the investigation of personal matters. This inspection report may provide the insurer with a wide range of personal information about a potential customer above and beyond what is on the application. In addition to an inspection report, the insurer may seek information on a potential customer from one of the cooperative information bureaus the insurance industry supports. The best known example is the Medical Information Bureau (MIB), which maintains centralized files on the physical condition of individuals who have applied for life insurance with member companies. In life insurance, one of the primary factors in assessing risk is an individual's health. Accordingly, it is no surprise that one of the most important sources of underwriting information is a physical exam. After examining a potential customer, a physician selected by the insurance company supplies the company with a detailed medical report. This report generally tells the company all it needs to know about the potential customer's present health.

The underwriting process is currently a manual process. It can involve numerous people including agents and doctors, and it can be very time-consuming. In view of the foregoing, it can be appreciated that a substantial need exists for systems and methods that can automate the underwriting process, improve decision-making, reduce the number of people involved and speed the overall process.

BRIEF SUMMARY OF THE INVENTION

Embodiments of the present invention relate to systems and methods for automating insurance underwriting by integrating information from multiple online databases and creating decision making advice useful to insurance underwriters. The first embodiment of the present invention is a system for insurance underwriting including a client, a database, and a server. The client allows information about an insurance applicant obtained from the applicant to be entered into the system and an underwriting decision determined for the insurance applicant to be returned from the system. The database contains information about the applicant not obtained from the applicant. It can include but is not limited to prescription drug histories, credit histories, motor vehicle records, and geocentric mortality indices. The server obtains applicant information entered through the client, retrieves applicant information contained in the database, calculates an insurance risk from the applicant information entered through the client and the applicant information contained in the database, translates the insurance risk into an underwriting decision and returns the underwriting decision to the client. The insurance risk calculated by the server and returned to the client may be a risk score, a risk classification, or both. This embodiment may further include a modifier entered into the system through the client that is used by the server to modify the insurance risk determined by the server and returned to the client.

A second embodiment is directed to a system for insurance underwriting based on prescription drug histories. The system includes a pharmacy benefits management database, a drug risk category database, a list of applicant characteristics, and a processor. The pharmacy benefits management database contains a list of prescription drugs for each individual in the pharmacy benefits management database and information about each prescription drug on the list including but not limited to a national drug code, a number of individual doses dispensed, and a date each of the individual doses were dispensed. The drug risk category database contains prescription drugs grouped into one or more specific disease categories that could contribute to premature death including but not limited to cardiovascular, cancer, smoking, hepatitis, HIV infection, diabetes, substance abuse, pulmonary, gastrointestinal, renal, psychological, neurological, endocrine, rheumatological, musculoskeletal, hematological, and a category for drugs not fitting into any of the other categories. The list of applicant characteristics includes but is not limited to one or more of sex, birth date, height, weight, and smoking status. The processor obtains an insurance applicant's list of prescription drugs, their dosages and dates they were dispensed from the pharmacy benefits management database, matches the list of prescription drugs to disease categories from the drug category database, calculates a risk score for the insurance applicant based on the disease categories matched and the list of prescription drugs dosages and dates, and modifies the risk score according to the list of applicant characteristics. This embodiment may further include a second processor that modifies the risk score calculated by the processor according to a modification scheme preset externally by an underwriter. This modification scheme may be a translation table that the second processor uses to translate the risk score calculated by the processor into a second risk score. Alternatively, this modification scheme may be a multiplier that the second processor multiples the risk score calculated by the processor by to produce a second risk score.

A third embodiment of the present invention is a method for calculating a prescription drug risk score for an insurance applicant. This method has several steps, although it will be appreciated that two or more of the following steps could be collapsed into a single step, or one or more of these steps may be broken up into even more steps. In a first step, a list of prescription drug for the insurance applicant is obtained from a pharmacy benefits management database. The pharmacy benefits management database contains a list of prescription drugs for each individual in the pharmacy benefits management database and information about each prescription drug on the list including but not limited to a national drug code, a number of individual doses dispensed, and a date each of the individual doses were dispensed. In a second step, a list of characteristics of the insurance applicant is obtained. The list of characteristics of the insurance applicant includes but is not limited to one or more of sex, birth date, height, weight, and smoking status. In a third step, the list of drug risk categories for the insurance applicant is obtained from a drug risk category database. The drug risk category database contains prescription drugs grouped into one or more specific disease categories that could contribute to premature death comprising cardiovascular, cancer, smoking, HIV infection, diabetes, substance abuse, pulmonary, hepatitis, gastrointestinal, renal, psychological, neurological, endocrine, rheumatological, musculoskeletal, hematological, and a category for drugs not fitting into any of the other categories. In a fourth step, a body mass index of the insurance applicant is calculated from the list of characteristics and if the body mass index cannot be calculated a default value is used. The body mass index of the insurance applicant is calculated by dividing the weight in kilograms by the height in meters squared. In a fifth step, the risk score of each of the drug risk categories for the insurance applicant is set to the default no risk value.

In a sixth step, one or more drug risk categories and a risk score of a prescription drug are determined from the list of prescription drugs by querying the drug risk category database with the insurance applicant's sex and a code for the prescription drug. In a seventh step, it is determined if the prescription drug is a different representation of a drug already processed. This step involves comparing drug categorization, dosage, and route of administration of the prescription drug with categorization, dosage, and routes of administration of all other drugs on a list of processed prescription drugs in order to determine if the prescription drug is a different representation of a drug already processed, discarding the prescription drug if it is a different representation of a drug already processed, and adding the prescription drug to the list of processed prescription drugs if it is not a different representation of a drug already processed. In an eighth step, it is determined if a drug category of the prescription drug is smoking. If it is, the smoking status of the insurance applicant is set to smoking. In a ninth step, a risk score of the prescription drug is modified based on the date of dispensing. This modification involves multiplying the risk score of the prescription drug by a modifier specified in a table containing different modifiers for different date ranges from the data of dispensing. In the tenth step, a risk score of the prescription drug is modified based on the refill pattern. This modification involves multiplying the risk score of the prescription drug by a modifier specified in a table containing different modifiers for different amounts of refills within different time periods.

In an eleventh step, the prescription drug is added to one or more drug risk categories for the insurance applicant. In a twelfth step, the risk scores of each drug risk category are calculated from the risk scores of prescription drugs in each drug risk category. This involves examining each prescription a drug risk category, finding a prescription drug with the highest risk score within the drug risk category, and adding to a risk score of the prescription drug with the highest risk score within the drug risk category a number of unique, non-zero risk prescription drugs in the drug risk category multiplied by a factor. In a thirteenth step, the drug risk category with a highest risk score is determined. In a fourteenth step, all prescription drugs found in the drug risk category with the highest risk score are removed from all other drug risk categories to prevent biasing from multiple purpose prescription drugs. The risk scores of drug categories from which prescription drugs were removed are then recalculated.

In the fifteenth step, a risk score of the drug risk category with the highest risk score is modified according to the smoking status of the insurance applicant and the drug risk category. One modification is multiplying the risk score of the drug risk category with the highest risk score by a constant if the drug risk category comprises cancer, pulmonary, cardiovascular, and diabetes and the smoking status of, the insurance applicant comprises smoking. Another modification is multiplying the risk score of the drug risk category with the highest risk score by a constant if the drug risk category comprises pulmonary and the smoking status of the insurance applicant comprises non-smoking. In a sixteenth step, a risk score of the drug risk category with the highest risk score is modified according to the body mass index of the insurance applicant and the drug risk category. One modification is multiplying the risk score of the drug risk category with the highest risk score by a constant if the drug risk category comprises cancer, HIV infection, smoking, neurological, musculoskeletal, endocrine, and hematological and the body mass index is less than 19 and greater than or equal to 17. A second modification is multiplying the risk score of the drug risk category with the highest risk score by a constant if the drug risk category comprises psychological and the body mass index is less than 19 and greater than or equal to 17. A third modification is multiplying the risk score of the drug risk category with the highest risk score by a constant if the drug risk category comprises cardiovascular and diabetes and the body mass index is less than 35 and greater than or equal to 32.

In a final step, a final prescription drug risk factor is calculated by multiplying the individual drug score of the second and third highest risk categories by constants and adding these values to the risk score of the drug risk category with the highest risk score. An exemplary calculation involves multiplying a drug score of the second highest risk category by 0.5 and a drug score of the third highest risk category by 0.25 and adding these values to the risk score of the drug risk category with the highest risk score.

This embodiment may include removing the risk contribution from the category for drugs not fitting into any of the other categories if the drug risk category with the highest risk score is not the category for drugs not fitting into any of the other categories. It may also include modifying the final prescription drug risk by a preset external factor set by an underwriter.

A fourth embodiment of the present invention is a system for insurance underwriting based on geocentric mortality data. This system includes a census database, a mortality database, a credit information database, a list of applicant characteristics, and a processor. The list of applicant characteristics includes but is not limited to one or more of sex, age, income, account balances, number of accounts, credit limits, original mortgage amount, and mortgage account balance. The processor obtains population data for a region of an insurance applicant from the census database, gathers mortality data for the region of the insurance applicant from the mortality database, retrieves financial data for the region of the insurance applicant from the credit information database, generates a mortality table for the region of the insurance applicant based on age, sex and financial information, and calculates a geocentric mortality risk score for the insurance applicant by comparing the list of applicant characteristic with the mortality table. This embodiment may include a second processor that modifies the geocentric mortality risk score calculated by the processor according to a modification scheme preset externally by an underwriter.

A fifth embodiment of the present invention is method for calculating a geocentric mortality risk score for an insurance applicant. This method also has, several steps. In a first step, a table containing populations of a region in which the insurance applicant lives grouped by age and sex is obtained. In a second step, a table containing the number of deaths that have occurred in the region in which the insurance applicant lives grouped by age and sex is obtained. In a third step, a table containing the financial data of households in the region in which the insurance applicant lives grouped by age and sex is obtained. In a fourth step, a mortality table for the region in which the insurance applicant lives based on financial data, age, and sex is generated. In a fifth step, a list of applicant characteristics about the insurance applicant is obtained. The list of applicant characteristics includes but is not limited to one or more of sex, age, income, account balances, number of accounts, credit limits, original mortgage amount, and mortgage account balance. In a sixth step, a geocentric mortality risk score is calculated by comparing the list of applicant characteristics to the mortality table. This embodiment may include an additional step of modifying the geocentric mortality risk score by a preset external factor set by an underwriter.

A sixth embodiment of the present invention is a system for insurance underwriting. The system includes but is not limited to a first processor that determines prescription drug risk, a second processor that determines geocentric mortality risk, a third processor that determines motor vehicle records risk, a fourth processor that determines credit information risk, a list of risks based on an applicant's application information, and a fifth processor. The fifth processor calculates an overall risk score by combining one or more of the risk scores of the first processor, the second processor, the third processor, the fourth processor, and the risks based on an applicant's application information. This embodiment may also contain a translation table used by the fifth processor to translate the risk scores of the first processor, the second processor, the third processor, the fourth processor and the risks based on an applicant's application information based on preset external factors set by the underwriter.

A seventh embodiment of the present invention is a method for calculating overall risk for an insurance applicant. In a first step, a first risk score is calculated based on a prescription drug history of the insurance applicant. In a second step, a second risk score for the insurance applicant is calculated based on a geocentric mortality data. In a third step, a third risk score is calculated based on a motor vehicle report history of the insurance applicant. In a fourth step, a fourth risk score is calculated based on a credit report for the insurance applicant. In a fifth step, additional risk parameters from the application data of the insurance applicant are gathered. In a final step, the overall risk for the insurance applicant is generated by combining one or more of the first risk score, the second risk score, the third risk score, the fourth risk score, and the additional risk parameters. This embodiment may also include the additional step of modifying the first risk score, the second risk score, the third risk, the fourth risk score, and the additional risk parameters based on a translation table provided as preset external data from an underwriter.

Figure 1:
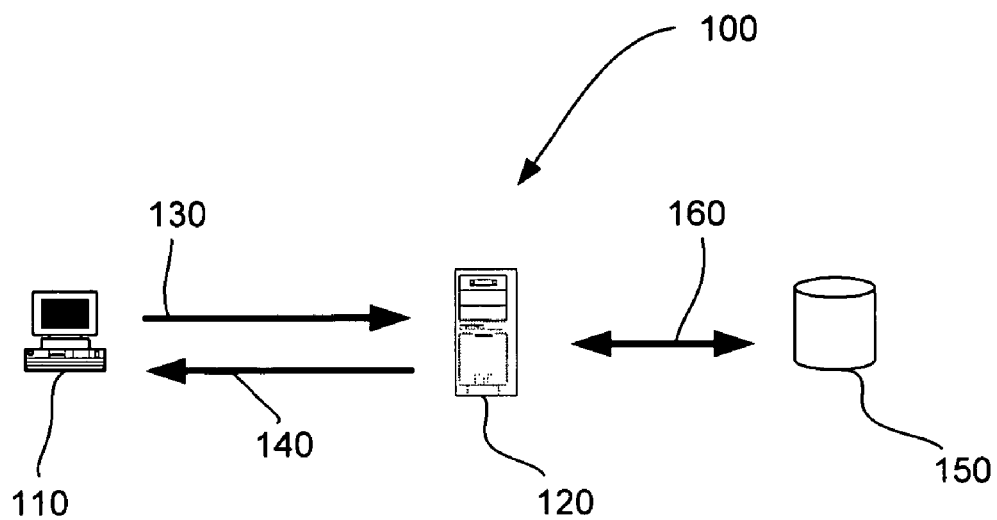
FIG. 1 is a schematic diagram showing two paths of communication between a client and a server in an insurance underwriting system containing a client, a database, and a server in accordance with an embodiment of the present invention.

Before one or more embodiments of the invention are described in detail, one skilled in the art will appreciate that the invention is not limited in its application to the details of construction, the arrangements of components, and the arrangement of steps set forth in the following detailed description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

FIG. 1 is a schematic diagram showing two paths of communication between a client and a server in an insurance underwriting system containing a client, a database, and a server in accordance with an embodiment of the present invention. In underwriting system 100, client 110 allows information about an insurance applicant obtained from the applicant to be entered into system 100. Exemplary methods of obtaining this information include an agent or underwriter receiving it orally from the applicant and entering it into system 100, an agent or underwriter transcribing it from a written application into system 100, or applicant entering the data directly where system 100 is an online system. In the these examples, the users of client 110 are an agent, an underwriter, or an applicant. This information is sent from client 110 to server 120 for processing via communications path 130. Client 110 also receives output from the system. This output is in the form of an underwriting decision determined by server 120 for the insurance applicant. An underwriting decision is the decision to write a policy for the applicant, to not write a policy for the applicant, or to refer the applicant to another underwriting process. The underwriting decision determined by server 120 for the insurance applicant is sent to client 110 via communications path 140.

Database 150 contains information about the applicant not obtained from the applicant. This information can include but is not limited to prescription drug histories, credit histories, motor vehicle records, and geocentric mortality indices. Database 150 is used to gather additional information about an applicant and to verify information already known about an applicant. Server 120 queries database 150 and receives this information via communications path 160.

Server 120 is the processor of underwriting system 100. Server 120 obtains applicant information entered through client 110. It retrieves applicant information contained in database 150. It calculated the insurance risk of the applicant from the applicant information entered through client 110 and the applicant information contained in database 140. Exemplary insurance risks provided by underwriting systems include a risk score and a risk classification. A risk score is a numeric value within a numeric range of risk. A risk classification is a grouping of applicants based on risk, as was described earlier. Server 120 translates the insurance risk into an underwriting decision. An exemplary server 120 translates a risk score into an underwriting decision by calling one range of risk scores a decision to underwrite a policy, a second range of risks scores a decision to refer the applicant to traditional underwriting, and a third range of risk scores a decision not to underwrite a policy. Similarly, an exemplary server 120 translates a risk classification through the use of a lookup table. For an uninsurable classification the underwriting decision is not to write a policy. For classifications substandard to preferred the decision is to underwrite the policy but at decreasing premiums for each of the classifications. Finally, server 120 returns the underwriting decision to client 110.

The method used by server 120 to determine the insurance risk varies depending on the database used. Also, if more than one database 150 is used, server 120 calculates the risk according to each database 150 and then calculates an overall insurance risk for the applicant. The use of one or many databases is under the control of the underwriter or agent in system 100. The underwriter or agent can then explore more than one scenario utilizing one or more databases. Server 120 then provides a type of programming interface for the underwriting process. When system 100 is configured as an online system to be accessed by applicants, the use of one or more databases is preset or varied according the information provided by the applicant.

Figure 2:
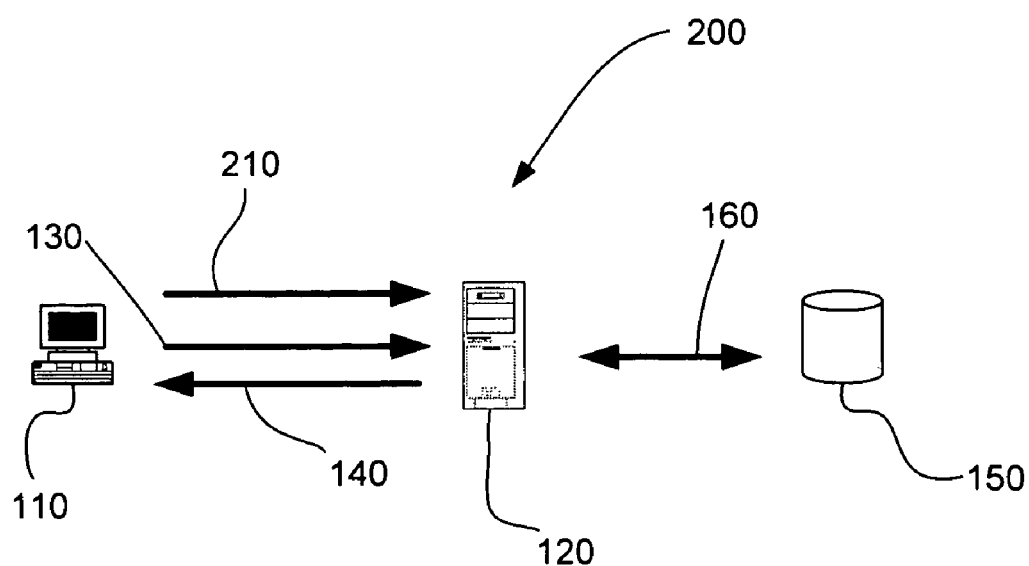
FIG. 2 is a schematic diagram showing three paths of communication between a client and a server in an insurance underwriting system containing a client, a database, and a server in accordance with an embodiment of the present invention.

FIG. 2 is a schematic diagram showing three paths of communication between a client and a server in an insurance underwriting system containing a client, a database, and a server in accordance with an embodiment of the present invention. In system 200, client 110 allows a modifier to be entered into the system that will modify the insurance risk determined by server 120 and returned to client 110. This modifier is entered via communication path 210. An exemplary modifier is a multiplier that is multiplied by the risk score to change its value. Another exemplary modifier is a translation table. A translation table is used to change the value of risk scores within a certain range to a specified value. Modifiers are used by underwriters to customize the underwriting results according to their experience. They are also used to enable the results to match the input parameters of other automated systems. If one or more databases 150 are used, then one or more modifiers are entered into the system through client 110. Communications paths 130, 140, 160, and 210 provide data communications via one or more computer networks.

Figure 3:
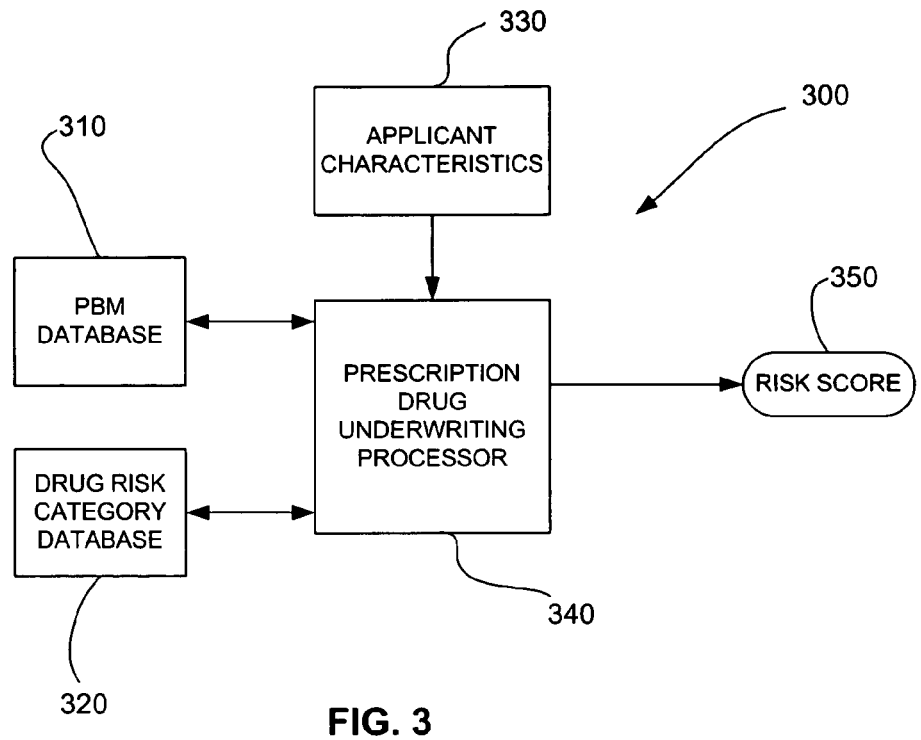
FIG. 3 is schematic diagram of a system for insurance underwriting based on prescription drug histories in accordance with an embodiment of the present invention.

FIG. 3 is schematic diagram of a system for insurance underwriting based on prescription drug histories in accordance with an embodiment of the present invention. System 300 includes pharmacy benefits management (PBM) database 310, drug risk category database 320, list of applicant characteristics 330, and prescription drug underwriting processor 340. PBM database 310 contains a list of prescription drugs for each individual in PBM database 310. It also includes information about each prescription drug on the list including but not limited to a national drug code, a number of individual doses dispensed, and a date each of the individual doses were dispensed. Drug risk category database 320 contains prescription drugs grouped into one or more specific disease categories that could contribute to premature death. These categories include but are not limited to cardiovascular, cancer, smoking, hepatitis, HIV infection, diabetes, substance abuse, pulmonary, gastrointestinal, renal, psychological, neurological, endocrine, rheumatological, musculoskeletal, hematological, and a category for drugs not fitting into any of the other categories. List of applicant characteristics 330 contains information about the applicant obtained from the applicant. This information is obtained during the application process and includes but is not limited to one or more of sex, birth date, height, weight, and smoking status. Processor 340 retrieves an insurance applicant's list of prescription drugs, their dosages and dates they were dispensed from the pharmacy benefits management database. It matches the list of prescription drugs to disease categories from drug category database 320. It calculates a risk score for the insurance applicant based on the disease categories matched and the list of prescription drugs dosages and dates dispensed. Finally, it modifies the risk score according to the list of applicant characteristics to produce the prescription drug risk score 350.

Figure 4:
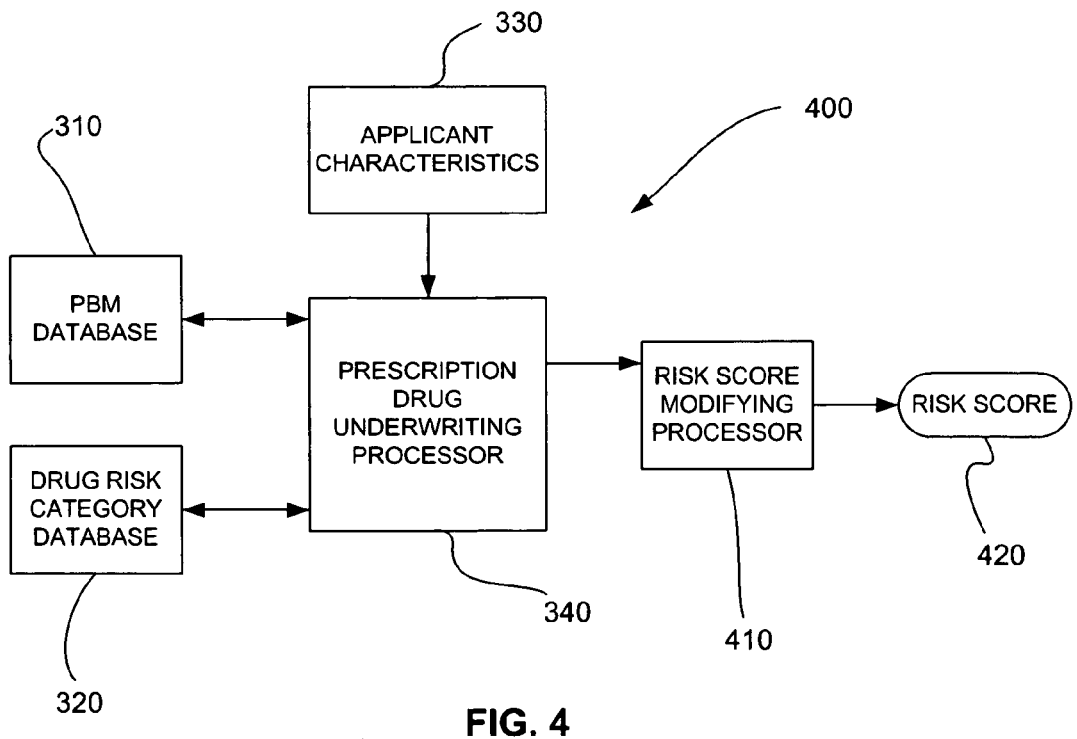
FIG. 4 is schematic diagram of a system for insurance underwriting based on prescription drug histories including a second processor that modifies the original risk score in accordance with an embodiment of the present invention.

FIG. 4 is schematic diagram of a system for insurance underwriting based on prescription drug histories including a second processor that modifies the original risk score in accordance with an embodiment of the present invention. In system 400, a second processor 410 modifies the risk score calculated by the processor 340 according to a modification scheme preset externally by an underwriter. This modification scheme may be a translation table that second processor 410 uses to translate the risk score calculated by processor 340 into a second risk score. Alternatively, this modification scheme may be a multiplier that second processor 410 multiples the risk score calculated by processor 340 by to produce second risk score 420.

Figure 5:
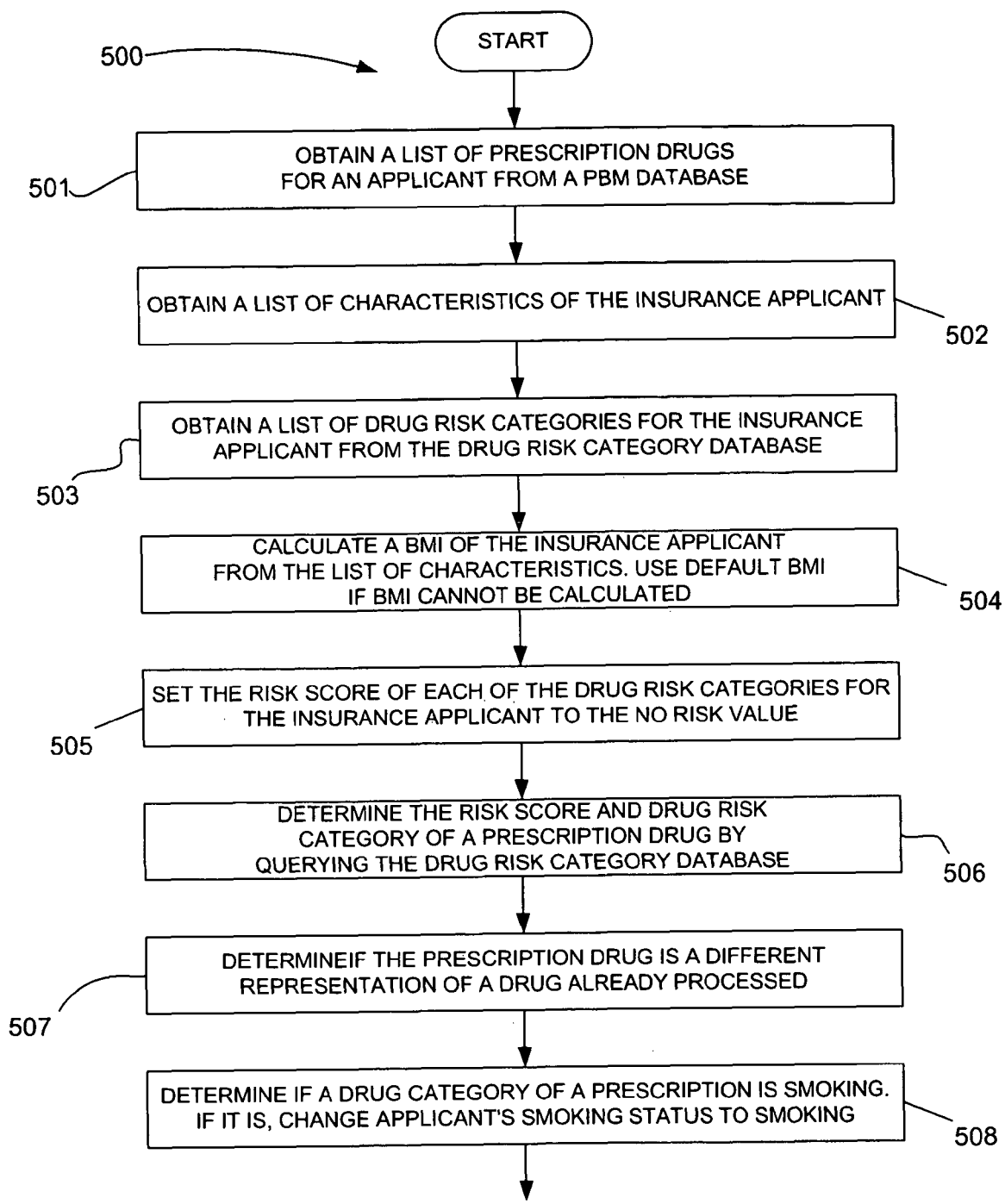
FIG. 5 is a flowchart showing a first series of steps of a method for calculating a prescription drug risk score for an insurance applicant in accordance with an embodiment of the present invention.

FIG. 5 is a flowchart showing a first series of steps of a method for calculating a prescription drug risk score for an insurance applicant in accordance with an embodiment of the present invention. A series of steps will be described with respect to this method, but those skilled in the art will appreciate that some of these steps may be combined or further broken down into yet additional steps.

In step 501 of method 500, a list of prescription drugs for the insurance applicant is obtained from a pharmacy benefits management database. The pharmacy benefits management database contains a list of prescription drugs for each individual in the pharmacy benefits management database and information about each prescription drug on the list including but not limited to a national drug code, a number of individual doses dispensed, and a date each of the individual doses were dispensed.

In step 502, a list of characteristics of the insurance applicant is obtained. The list of characteristics of the insurance applicant includes but is not limited to one or more of sex, birth date, height, weight, and smoking status.

In step 503, the list of drug risk categories for the insurance applicant is obtained from a drug risk category database. The drug risk category database contains prescription drugs grouped into one or more specific disease categories that could contribute to premature death comprising cardiovascular, cancer, smoking, HIV infection, diabetes, substance abuse, pulmonary, hepatitis, gastrointestinal, renal, psychological, neurological, endocrine, rheumatological, musculoskeletal, hematological, and a category for drugs not fitting into any of the other categories.

In step 504, a body mass index of the insurance applicant is calculated from the list of characteristics and if the body mass index cannot be calculated a default value is used. An exemplary default value is 25. The body mass index of the insurance applicant is calculated by dividing the weight in kilograms by the height in meters squared.

In step 505, the risk score of each of the drug risk categories for the insurance applicant is set to the default no risk value. This is an initialization step since the drug risk categories are used later to calculate the final risk value.

In step 506, one or more drug risk categories and a risk score of a prescription drug are determined from the list of prescription drugs by querying the drug risk category database with the insurance applicant's sex and a code for the prescription drug. The national drug code of each prescription drug is used to query the drug risk category database. The database is also segregated with respect to gender, so the sex of the applicant is also used in the query. From querying the drug risk category database the initial risk score of each drug is found. The category or categories to which each prescription drug belongs is also determined. The list of drug risk categories includes but is not limited to cardiovascular, cancer, smoking, hepatitis, HIV infection, diabetes, substance abuse, pulmonary, gastrointestinal, renal, psychological, neurological, endocrine, rheumatological, musculoskeletal, hematological, and a category for drugs not fitting into any of the other categories. Exemplary risk values for a prescription are from a range between 0 and 90 and including 0 and 90, where 0 is no risk and 90 is the highest risk possible for a single drug.

In step 507, it is determined if the prescription drug is a different representation of a drug already processed. Obviously, drugs with the same national drug code are the same drug, but different manufacturers and especially generic drugs may be identical, yet have different codes. This step involves comparing drug categorization, dosage, and route of administration of the prescription drug with categorization, dosage, and routes of administration of all other drugs on a list of processed prescription drugs in order to determine if the prescription drug is a different representation of a drug already processed. A prescription drug is discarded if it is a different representation of a drug already processed. Drugs not already processed are added to the list of processed prescription drugs.

In step 508, it is determined if a drug category of the prescription drug is smoking. If it is, the smoking status of the insurance applicant is set to smoking. Exemplary values for the smoking status of an applicant include smoking, non-smoking, and prior smoking.

Figure 6:
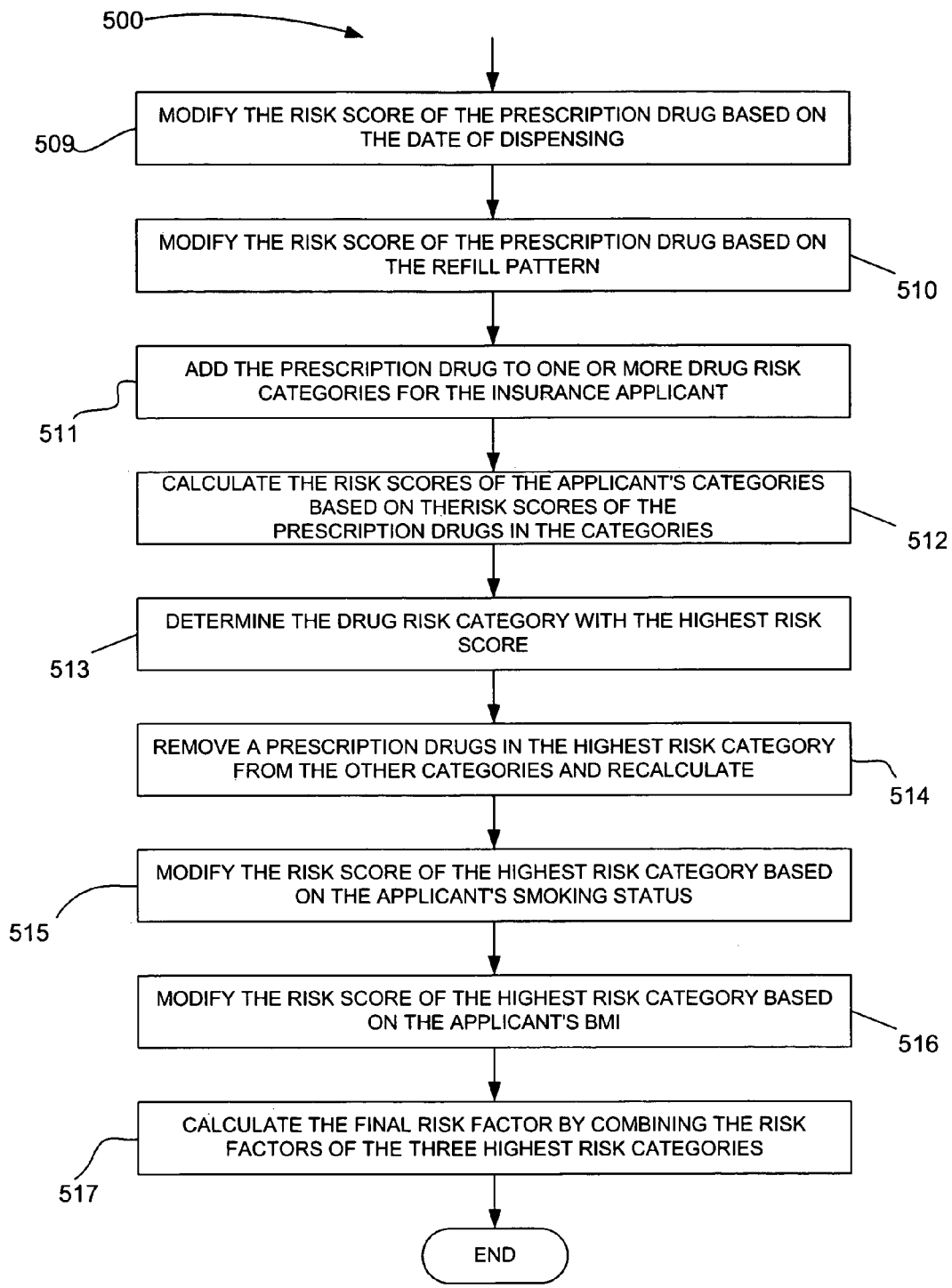
FIG. 6 is a flowchart showing a second series of steps of a method for calculating a prescription drug risk score for an insurance applicant in accordance with an embodiment of the present invention.

FIG. 6 is a flowchart showing a second series of steps of a method for calculating a prescription drug risk score for an insurance applicant in accordance with an embodiment of the present invention.

In step 509 of method 500, a risk score of the prescription drug is modified based on the date of dispensing. This modification involves multiplying the risk score of the prescription drug by a modifier specified in a table containing different modifiers for different date ranges from the data of dispensing. An exemplary modifier for a prescription drug not dispensed in the past two years is 0.50. An exemplary modifier for a prescription drug dispensed within the past two years is 0.75.

In the step 510, a risk score of the prescription drug is modified based on the refill pattern. This modification involves multiplying the risk score of the prescription drug by a modifier specified in a table containing different modifiers for different amounts of refills within different time periods. An exemplary modifier for a prescription drug with up to 6 refills in a two year period is 0.75. An exemplary modifier for a prescription drug with between 6 and 12 refills in a two year period is 0.75.

In step 511, the prescription drug is added to one or more drug risk categories for the insurance applicant.

In step 512, the risk scores of each drug risk category are calculated from the risk scores of prescription drugs in each drug risk category. This involves examining each prescription a drug risk category and finding the prescription drug with the highest risk score within the drug risk category. The risk score of the drug risk category is then calculated by counting the other of unique, non-zero risk prescription drugs in the drug risk category, multiplying this count by a factor, and adding this value to the risk score of the prescription drug with the highest risk score within the drug risk category.

In step 513, the drug risk category with a highest risk score is determined. This is determined by comparing the risk scores of all the drug risk categories for the applicant.

In step 514, all prescription drugs found in the drug risk category with the highest risk score are removed from all other drug risk categories to prevent biasing from multiple purpose prescription drugs. The risk scores of drug categories from which prescription drugs were removed are then recalculated.

In step 515, a risk score of the drug risk category with the highest risk score is modified according to the smoking status of the insurance applicant and the drug risk category. One modification is multiplying the risk score of the drug risk category with the highest risk score by a constant if the drug risk category comprises cancer, pulmonary, cardiovascular, and diabetes and the smoking status of the insurance applicant comprises smoking. Another modification is multiplying the risk score of the drug risk category with the highest risk score by a constant if the drug risk category comprises pulmonary and the smoking status of the insurance applicant comprises non-smoking.

In step 516, a risk score of the drug risk category with the highest risk score is modified according to the body mass index of the insurance applicant and the drug risk category. One modification is multiplying the risk score of the drug risk category with the highest risk score by a constant if the drug risk category comprises cancer, HIV infection, smoking, neurological, musculoskeletal, endocrine, and hematological and the body mass index is less than 19 and greater than or equal to 17. A second modification is multiplying the risk score of the drug risk category with the highest risk score by a constant if the drug risk category comprises psychological and the body mass index is less than 19 and greater than or equal to 17. A third modification is multiplying the risk score of the drug risk category with the highest risk score by a constant if the drug risk category comprises cardiovascular and diabetes and the body mass index is less than 35 and greater than or equal to 32.

In step 517, a final prescription drug risk factor is calculated by multiplying the individual drug score of the second and third highest risk categories by constants and adding these values to the risk score of the drug risk category with the highest risk score. An exemplary calculation involves multiplying a drug score of the second highest risk category by 0.5 and a drug score of the third highest risk category by 0.25 and adding these values to the risk score of the drug risk category with the highest risk score.

Method 500 can include a number of additional steps. One step is modifying a risk score of the prescription drug based on a dosage pattern. This involves multiplying the risk score of the prescription by a modifier specified in a table containing different modifiers for different dosages of the prescription drug. An exemplary dosage multiplier is 0.70 for a very low dose. Another exemplary multiplier is 0.90 for a high dose.

Another additional step is removing the risk contribution from the category for drugs not fitting into any of the other categories, if the drug risk category with the highest risk score is not the category for drugs not fitting into any of the other categories.

A final additional step is modifying the final prescription drug risk by a preset external factor set by an underwriter.

Figure 7:
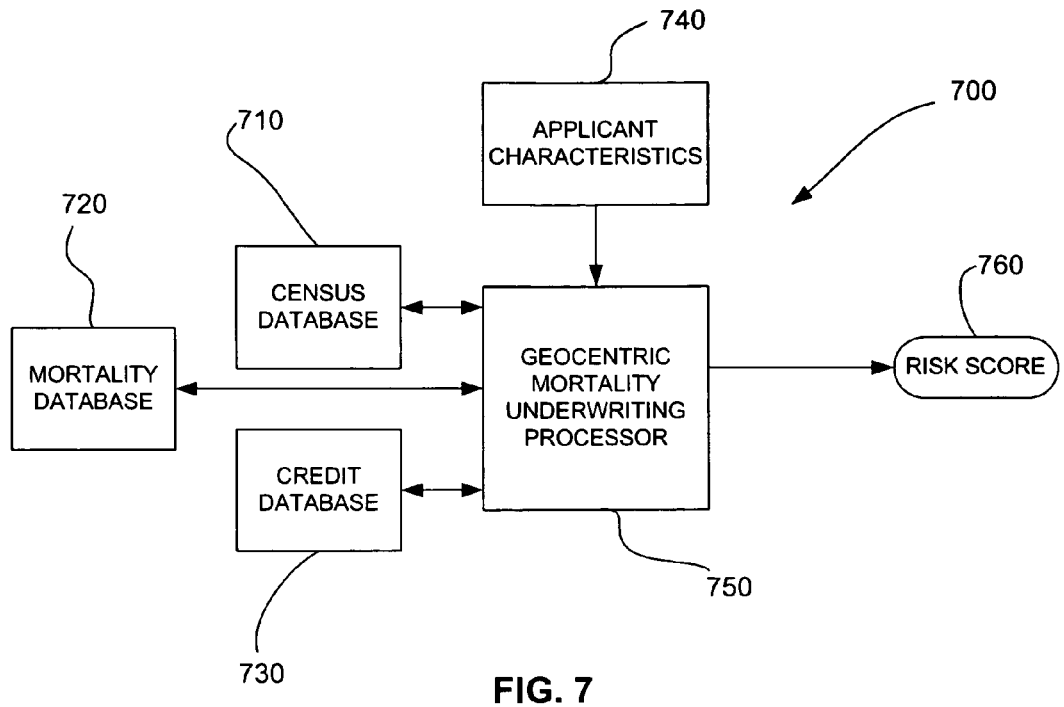
FIG. 7 is schematic diagram of a system for insurance underwriting based on geocentric mortality data in accordance with an embodiment of the present invention.

FIG. 7 is schematic diagram of a system for insurance underwriting based on geocentric mortality data in accordance with an embodiment of the present invention. System 700 includes census database 710, mortality database 720, credit information database 730, a list of applicant characteristics 740, and geocentric mortality processor 750. List of applicant characteristics 740 includes but is not limited to one or more of sex, age, income, account balances, number of accounts, credit limits, original mortgage amount, and mortgage account balance. Processor 750 obtains population data for a region of an insurance applicant from the census database. It gathers mortality data for the region of the insurance applicant from the mortality database. It retrieves financial data for the region of the insurance applicant from the credit information database. It generates a mortality table for the region of the insurance applicant based on age, sex and financial information. Finally, it calculates geocentric mortality risk score 760 for the insurance applicant by comparing the list of applicant characteristic with the mortality table.

Figure 8:
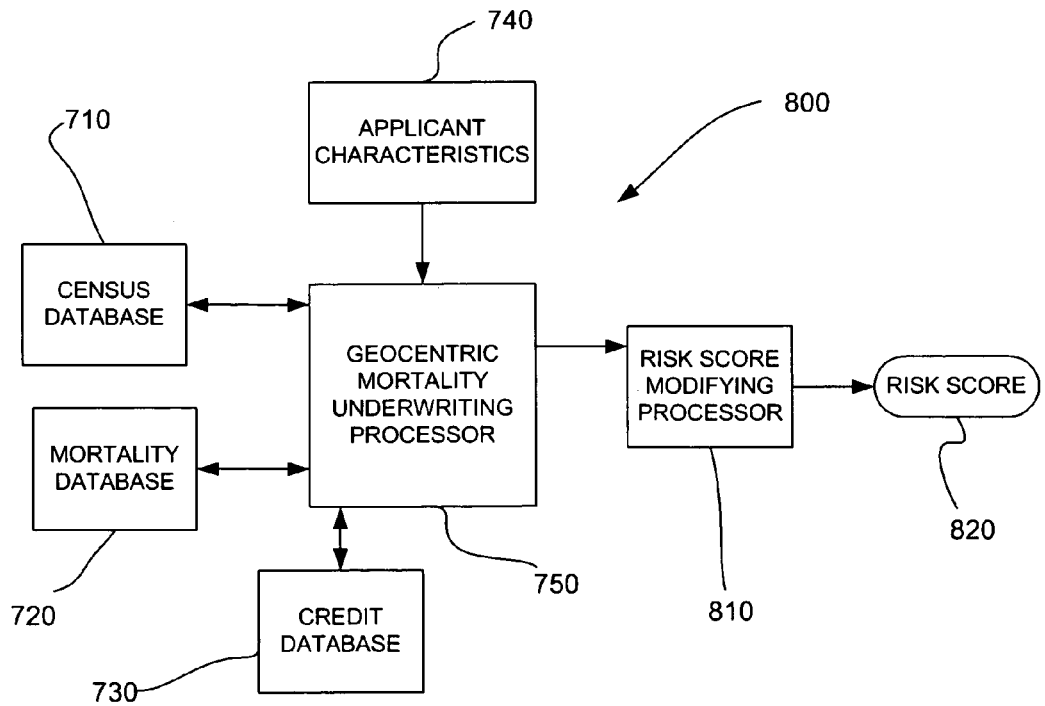
FIG. 8 is schematic diagram of a system for insurance underwriting based on geocentric mortality data including a second processor in accordance with an embodiment of the present invention.

FIG. 8 is schematic diagram of a system for insurance underwriting based on geocentric mortality data including a second processor in accordance with an embodiment of the present invention. System 800 includes second processor 810 that modifies the geocentric mortality risk score calculated by processor 750 according to a modification scheme preset externally by an underwriter. System 800 then produced modified geocentric mortality risk score 820.

Figure 9:
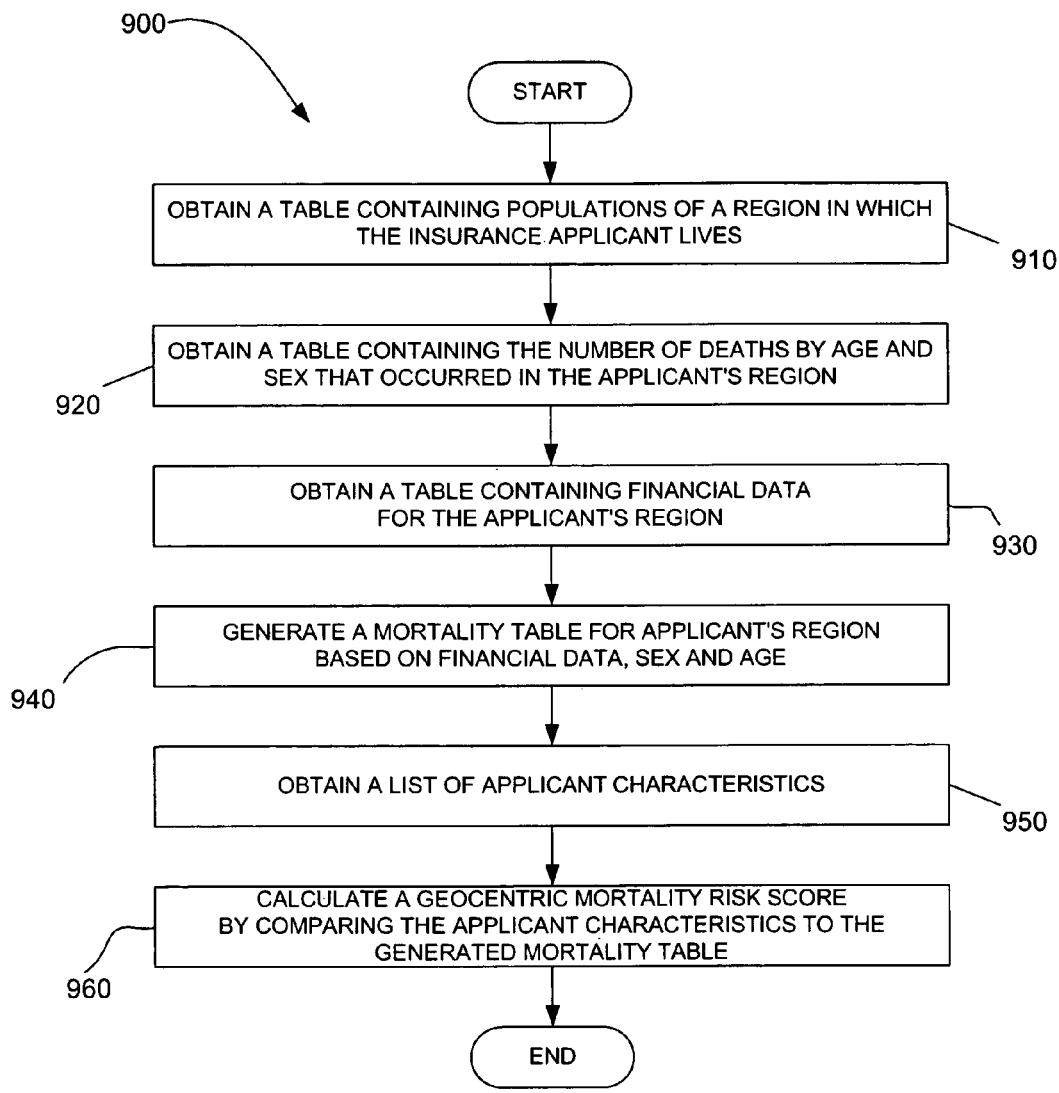
FIG. 9 is a flowchart showing a method for calculating a geocentric mortality risk score for an insurance applicant in accordance with an embodiment of the present invention.

FIG. 9 is a flowchart showing a method for calculating a geocentric mortality risk score for an insurance applicant in accordance with an embodiment of the present invention.

In step 910, a table containing populations of a region in which the insurance applicant lives grouped by age and sex is obtained.

In the step 920, a table containing the number of deaths that have occurred in the region in which the insurance applicant lives grouped by age and sex is obtained.

In the step 930, a table containing the financial data of households in the region in which the insurance applicant lives grouped by age and sex is obtained.

In step 940, a mortality table for the region in which the insurance applicant lives based on financial data, age, and sex is generated.

In step 950, a list of applicant characteristics about the insurance applicant is obtained. The list of applicant characteristics includes but is not limited to one or more of sex, age, income, account balances, number of accounts, credit limits, original mortgage amount, and mortgage account balance.

In step 960, a geocentric mortality risk score is calculated by comparing the list of applicant characteristics to the mortality table.

An additional step for method 900 is modifying the geocentric mortality risk score by a preset external factor set by an underwriter. This step allows the underwriter to customize the results of the method.

Figure 10:
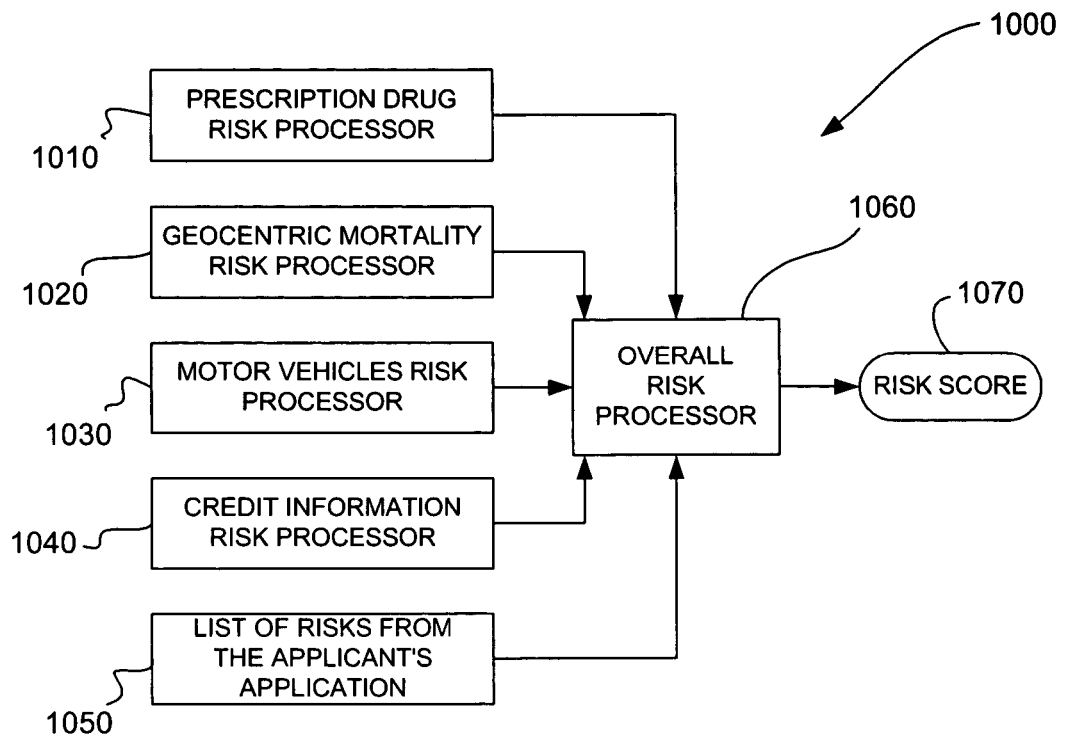
FIG. 10 is schematic diagram of a system for insurance underwriting based on prescription drug risk, geocentric mortality risk, motor vehicle records risk, credit information risk, and risks based on an applicant's application information in accordance with an embodiment of the present invention.

FIG. 10 is schematic diagram of a system for insurance underwriting based on prescription drug risk, geocentric mortality risk, motor vehicle records risk, credit information risk, and risks based on an applicant's application information in accordance with an embodiment of the present invention. System 1000, includes but is not limited to first processor 1010 that determines prescription drug risk, a second processor 1020 that determines geocentric mortality risk, a third processor 1030 that determines motor vehicle records risk, a fourth processor 1040 that determines credit information risk, list of risks based on an applicant's application information 1050, and fifth processor 1060. Exemplary motor vehicle records risk is calculated based on violations or accidents. Exemplary credit information risk is calculated based on net worth, outstanding loans, account balances, or unpaid bills. Exemplary risks based on an applicant's application information include occupation, avocation, and whether or not the applicant is a smoker. Fifth processor 1060 calculates overall risk score 1070 by combining one or more of the risk scores of the first processor 1010, second processor 1020, third processor 1030, fourth processor 1040, and list of risks based on an applicant's application information 1050. An exemplary method of combining the risk scores is to add them with or without first applying weighting factors.

Figure 11:
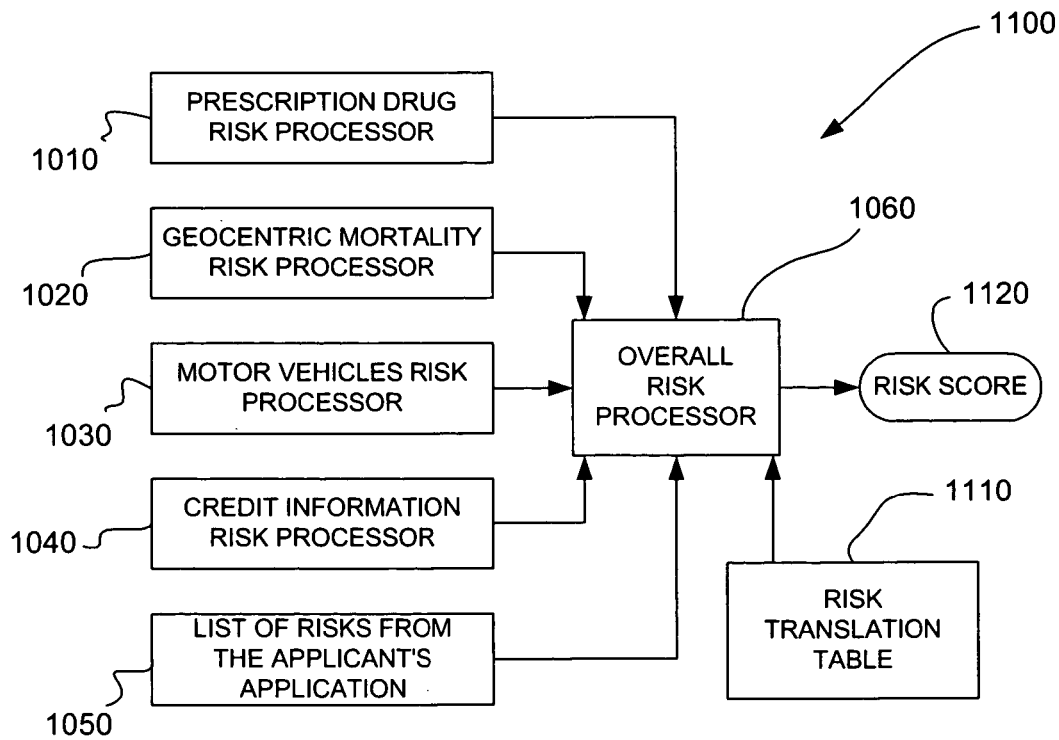
FIG. 11 is schematic diagram of a system for insurance underwriting based on prescription drug risk, geocentric mortality risk, motor vehicle records risk, credit information risk, risks based on an applicant's application information, and a translation table in accordance with an embodiment of the present invention.

FIG. 11 is schematic diagram of a system for insurance underwriting based on prescription drug risk, geocentric mortality risk, motor vehicle records risk, credit information risk, risks based on an applicant's application information, and a translation table in accordance with an embodiment of the present invention. System 1100 contains translation table 1110 used by fifth processor 1060 to translate the risk scores of the first processor, the second processor, the third processor, the fourth processor and the risks based on an applicant's application information based on preset external factors set by the underwriter. System 1100 then produces modified overall risk score 1120. An exemplary translation table translates a prescription drug risk in the range 41 to 45, to 100. In this way, an individual processor's range of 0 to 90 can be converted to an overall risk range of 0 to 250, for example.

Figure 12:
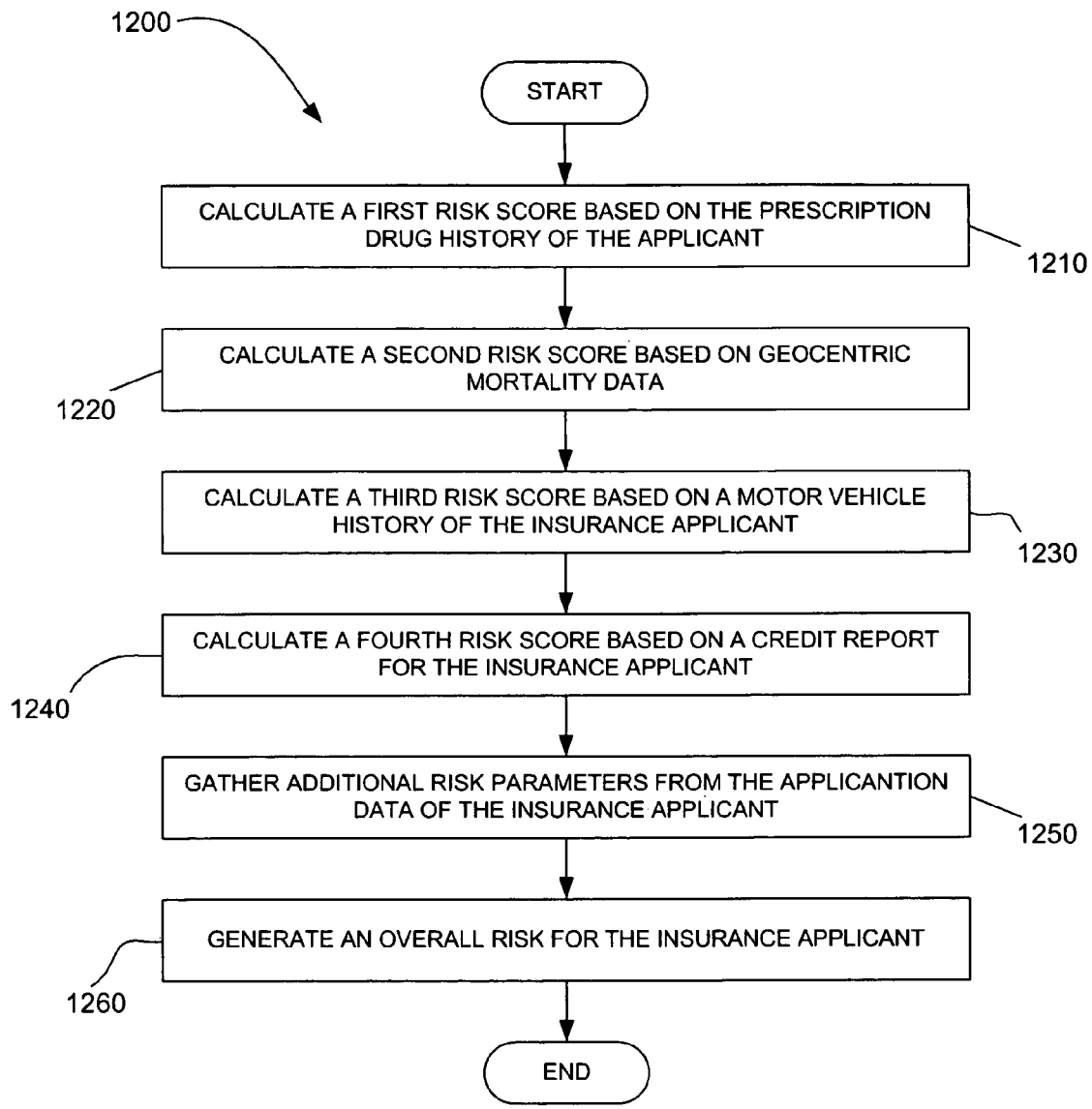
FIG. 12 is a flowchart of a method for calculating overall risk for an insurance applicant based on prescription drug risk, geocentric mortality risk, motor vehicle records risk, credit information risk, and risks based on an applicant's application information in accordance with an embodiment of the present invention.

FIG. 12 is a flowchart of a method for calculating overall risk for an insurance applicant based on prescription drug risk, geocentric mortality risk, motor vehicle records risk, credit information risk, and risks based on an applicant's application information in accordance with an embodiment of the present invention.

In step 1210, a first risk score is calculated based on a prescription drug history of the insurance applicant.

In step 1220, a second risk score for the insurance applicant is calculated based on a geocentric mortality data.

In step 1230, a third risk score is calculated based on a motor vehicle report history of the insurance applicant.

In step 1240, a fourth risk score is calculated based on a credit report for the insurance applicant.

In step 1250, additional risk parameters from the application data of the insurance applicant are gathered.

In step 1260, the overall risk for the insurance applicant is generated by combining one or more of the first risk score, the second risk score, the third risk score, the fourth risk score, and the additional risk parameters.

An additional step of method 1200 is modifying the first risk score, the second risk score, the third risk, the fourth risk score, and the additional risk parameters based on a translation table provided as preset external data from an underwriter.

Systems and methods in accordance with embodiments of the present invention disclosed herein can advantageously improve the speed of insurance underwriting and reduce the overall cost. Such systems and methods also provide agents and underwriters with a customizable tool that can be used to explore different underwriting scenarios.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for insurance underwriting, comprising:
    at least one database containing information about an insurance applicant, wherein the information about the insurance applicant includes insurance application information obtained from the insurance applicant and additional information not obtained from the insurance applicant, wherein the additional information not obtained from the insurance applicant comprises a plurality of prescription drugs dispensed to the insurance applicant;
    a drug risk category database that groups the plurality of prescription drugs dispensed to the insurance applicant within a drug risk category; and
    a server in communication with the at least one database and a client computer used to enter the insurance application information obtained from the insurance applicant, wherein the server is configured to:
        retrieve the insurance application information obtained from the insurance applicant and the additional information not obtained from the insurance applicant from the database;
        determine a plurality of risk scores for the insurance applicant from the insurance application information and the additional information retrieved from the database, wherein the plurality of risk scores include an initial prescription drug risk score, a geocentric mortality risk score, a motor vehicle records risk score, and a credit information risk score;

modify at least the initial prescription drug risk score according to a predetermined modification scheme established by an external underwriter, wherein to modify the initial prescription drug risk score according to the predetermined modification scheme, the server is further configured to:

determine a plurality of risk scores for the plurality of prescription drugs grouped within the drug risk category, wherein the server identifies one of the plurality of prescription drugs grouped within the drug risk category having a highest risk score;

multiply a remaining number of the plurality of prescription drugs grouped within the drug risk category having unique, non-zero risk scores by a predetermined factor; and add the highest risk score associated with the identified prescription drug to a value obtained from multiplying the remaining number of the plurality of prescription drugs by the predetermined factor, wherein the server adds the highest risk score and the obtained value to calculate a risk score for the drug risk category, and wherein the server modifies the initial prescription drug score based on the risk score calculated for the drug risk category;

calculate an overall risk score for the insurance applicant, wherein the server combines the modified prescription drug risk score with one or more of the geocentric mortality risk score, the motor vehicle records risk score, or the credit information risk score to calculate the overall risk score for the insurance applicant;

translate the overall risk score into an insurance underwriting decision for the insurance applicant; and return the insurance underwriting decision for the insurance applicant to the client computer.

2. The system of claim 1, wherein the additional information in the at least one database not obtained from the insurance applicant comprises one or more of a prescription drug history, a credit history, a motor vehicle record, or a geocentric mortality index.

3. The system of claim 1, wherein the insurance underwriting decision comprises a decision to underwrite an insurance policy for the insurance applicant in response to the overall risk score having a numeric value within a first numeric risk range, a decision to refer to the insurance applicant to traditional underwriting in response to the overall risk score having a numeric value within a second numeric risk range, and a decision to not underwrite the insurance policy for the insurance applicant in response to the overall risk score having a numeric value within a third numeric risk range.

4. The system of claim 1, wherein the server is further configured to modify the overall risk score calculated for the insurance applicant according to the predetermined modification scheme established by the external underwriter.

5. A system for insurance underwriting, comprising:

at least one database containing information about an insurance applicant, wherein the information about the insurance applicant includes insurance application information obtained from the insurance applicant and additional information not obtained from the insurance applicant, wherein the additional information not obtained from the insurance applicant comprises a plurality of prescription drugs dispensed to the insurance applicant;

a drug risk category database that groups the plurality of prescription drugs dispensed to the insurance applicant within a drug risk category;

a first processor configured to determine an initial prescription drug risk score for the insurance applicant from the insurance application information in the database;

a second processor configured to determine a geocentric mortality risk score for the insurance applicant from the insurance application information in the database;

a third processor configured to determine a motor vehicle records risk score for the insurance applicant from the insurance application information in the database;

a fourth processor configured to determine a credit information risk score for the insurance applicant from the insurance application information in the database; and a fifth processor configured to:

modify at least the initial prescription drug risk score according to a predetermined modification scheme established by an external underwriter, wherein to modify the initial prescription drug risk score according to the predetermined modification scheme, the fifth processor is further configured to:

determine a plurality of risk scores for the plurality of prescription drugs grouped within the drug risk category, wherein the fifth processor identifies one of the plurality of prescription drugs grouped within the drug risk category having a highest risk score;

multiply a remaining number of the plurality of prescription drugs grouped within the drug risk category having unique, non-zero risk scores by a predetermined factor; and add the highest risk score associated with the identified prescription drug to a value obtained from multiplying the remaining number of the plurality of prescription drugs by the predetermined factor, wherein the fifth processor adds the highest risk score and the obtained value to calculate a risk score for the drug risk category, and wherein the fifth processor modifies the initial prescription drug score based on the risk score calculated for the drug risk category;

combine the modified prescription drug risk score with one or more of the geocentric mortality risk score, the motor vehicle records risk score, or the credit information risk score to calculate an overall risk score for the insurance applicant;

translate the overall risk score into an insurance underwriting decision for the insurance applicant.

6. The system of claim 5, wherein the insurance underwriting decision comprises a decision to underwrite an insurance policy for the insurance applicant in response to the overall risk score having a numeric value within a first numeric risk range, a decision to refer to the insurance applicant to traditional underwriting in response to the overall risk score having a numeric value within a second numeric risk range, and a decision to not underwrite the insurance policy for the insurance applicant in response to the overall risk score having a numeric value within a third numeric risk range.

7. A method for insurance underwriting, comprising:

storing information about an insurance applicant in at least one database, wherein the information about the insurance applicant includes insurance application information obtained from the insurance applicant;

storing additional information about the insurance applicant not obtained from the insurance applicant in a drug risk category database, wherein the additional information not obtained from the insurance applicant includes a plurality of prescription drugs dispensed to the insurance applicant, and wherein the drug risk category database groups the plurality of prescription drugs dispensed to the insurance applicant within a drug risk category;

determining, on a computer server, an initial prescription drug risk score for the insurance applicant from a prescription drug history associated with the insurance application information obtained from the insurance applicant and stored in the database;

determining, on the computer server, a geocentric mortality risk score for the insurance applicant from geocentric mortality data associated with the insurance application information obtained from the insurance applicant and stored in the database;

determining, on the computer server, a motor vehicle records risk score for the insurance applicant from a motor vehicle report history associated with the insurance application information obtained from the insurance applicant and stored in the database;

determining, on the computer server, a credit information risk score for the insurance applicant from a credit report associated with the insurance application information obtained from the insurance applicant and stored in the database;

modifying, on the computer server, at least the initial prescription drug risk score according to a predetermined modification scheme established by an external underwriter, wherein modifying the initial prescription drug risk score according to the predetermined modification scheme includes:

determining, on the computer server, a plurality of risk scores for the plurality of prescription drugs grouped within the drug risk category, wherein the computer server identifies one of the plurality of prescription drugs grouped within the drug risk category having a highest risk score;

multiplying, on the computer server, a remaining number of the plurality of prescription drugs grouped within the drug risk category having unique, non-zero risk scores by a predetermined factor; and adding, on the computer server, the highest risk score associated with the identified prescription drug to a value obtained from multiplying the remaining number of the plurality of prescription drugs by the predetermined factor, wherein the computer server adds the highest risk score and the obtained value to calculate a risk score for the drug risk category, and wherein the computer server modifies the initial prescription drug score based on the risk score calculated for the drug risk category;

calculating, on the computer server, an overall risk score for the insurance applicant, wherein calculating the overall risk score for the insurance applicant includes combining the modified prescription drug risk score with one or more of the geocentric mortality risk score, the motor vehicle records risk score, or the credit information risk score; and translating the overall risk score into an insurance underwriting decision for the insurance applicant.

8. The method of claim 7, wherein the insurance underwriting decision comprises a decision to underwrite an insurance policy for the insurance applicant in response to the overall risk score having a numeric value within a first numeric risk range, a decision to refer to the insurance applicant to traditional underwriting in response to the overall risk score having a numeric value within a second numeric risk range, and a decision to not underwrite the insurance policy for the insurance applicant in response to the overall risk score having a numeric value within a third numeric risk range.

9. The system of claim 1, wherein the additional information in the at least one database not obtained from the insurance applicant comprises at least one prescription drug dispensed to the insurance applicant.

10. The system of claim 9, wherein the server is further configured to query the drug risk category database with a gender for the insurance applicant and a national drug code for the prescription drug dispensed to the insurance applicant, wherein the server queries the drug risk category database with the gender for the insurance applicant and the national drug code for the prescription drug dispensed to the insurance applicant to determine the initial prescription drug risk score for the insurance applicant.

11. The system of claim 10, wherein the server is further configured to:

determine a date when the prescription drug was dispensed to the insurance applicant, wherein the server determines the date when the prescription drug was dispensed to the insurance applicant to identify a date range modifier in the predetermined modification; and multiply the initial prescription drug risk score by the identified date range modifier, wherein the modified prescription drug risk score comprises the initial prescription drug risk score multiplied by the identified date range modifier.

12. The system of claim 10, wherein the server is further configured to:

determine a number of refills dispensed to the insurance applicant for the prescription drug, wherein the server determines the number of refills dispensed to the insurance applicant to identify a refill pattern modifier in the predetermined modification; and multiply the initial prescription drug risk score by the identified refill pattern modifier, wherein the modified prescription drug risk score comprises the initial prescription drug risk score multiplied by the identified refill pattern modifier.

13. The system of claim 10, wherein the server is further configured to:

determine a dosage for the prescription drug dispensed to the insurance applicant, wherein the server determines the dosage for the prescription drug to identify a dosage pattern modifier in the predetermined modification scheme; and multiply the initial prescription drug risk score by the identified dosage pattern modifier, wherein the modified prescription drug risk score comprises the initial prescription drug risk score multiplied by the identified dosage pattern modifier.

14. The system of claim 9, wherein the server is further configured to:

query a drug risk category database with a national drug code for the prescription drug dispensed to the insurance applicant, wherein the drug risk category database groups a plurality of prescription drugs into a plurality of disease categories that could contribute to premature death; and determine a drug risk category for the prescription drug dispensed to the insurance applicant from one or more of the plurality of disease categories matching the prescription drug dispensed to the insurance applicant.

15. The system of claim 14, wherein the server is further configured to assign a smoking status to the insurance applicant in response to the determined drug risk category comprising a smoking drug risk category.

16. The system of claim 1, wherein one or more of the initial prescription drug risk score or the modified prescription drug risk score are based on the risk score calculated for the drug risk category.

17. The system of claim 1, wherein the additional information in the at least one database not obtained from the insurance applicant comprises a plurality of prescription drugs dispensed to the insurance applicant, and wherein a drug risk category database groups the plurality of prescription drugs dispensed to the insurance applicant within a plurality of drug risk categories.

18. The system of claim 17, wherein the server is further configured to:
determine that the plurality of prescription drugs dispensed to the insurance applicant include multiple different representations of one prescription drug; and
discard all but one of the multiple different representations of the one prescription drug from the plurality of prescription drugs dispensed to the insurance applicant.

19. The system of claim 17, wherein the server is further configured to calculate a plurality of initial risk scores for the plurality of drug risk categories that group the plurality of prescription drugs dispensed to the insurance applicant, wherein the server identifies one of the plurality of drug risk categories having a highest initial risk score.

20. The system of claim 19, wherein the server is further configured to:
identify any of the plurality of prescription drugs grouped within the identified drug risk category having the highest initial risk score that are further grouped within other ones of the plurality of drug risk categories; and
remove the identified prescription drugs from the other drug risk categories, wherein the server remove the identified prescription drugs from the other drug risk categories to prevent biasing from multiple purpose prescription drugs.

21. The system of claim 19, wherein the server is further configured to:
determine a smoking status assigned to the insurance applicant, wherein the server determines the smoking status assigned to the insurance applicant to identify a smoking constant in the predetermined modification scheme; and
multiply the initial risk score associated with the drug risk category having the highest initial risk score by the identified smoking constant, wherein the modified prescription drug risk score comprises the initial risk score associated with the drug risk category having the highest initial risk score multiplied by the identified smoking constant.

22. The system of claim 19, wherein the server is further configured to:
determine a weight in kilograms and a height in meters for the insurance applicant from the insurance application information obtained from the insurance applicant;
calculate a body mass index for the insurance applicant from the weight in kilograms and the height in meters determined for the insurance applicant, wherein the calculated body mass index includes the weight in kilograms divided by the height in meters squared;
identify a body mass index constant in the predetermined modification scheme from the body mass index calculated for the insurance applicant; and
multiply the initial risk score associated with the drug risk category having the highest initial risk score by the identified body mass index constant, wherein the modified prescription drug risk score comprises the initial risk score associated with the drug risk category having the highest initial risk score multiplied by the identified body mass index constant.

23. The system of claim 19, wherein the server is further configured to:
identify one of the plurality of drug risk categories having a second highest initial risk score and one of the plurality of drug risk categories having a third highest initial risk score;
multiply the second highest initial risk score by a first constant;
multiply the third highest initial risk score by a second constant, wherein the second constant comprises a lower value than the first constant; and
add the highest initial risk score to the second highest initial risk score multiplied by the first constant and the third highest initial risk score multiplied by the second constant, wherein the modified prescription drug risk score comprises the highest initial risk score added to the multiplied second highest initial risk score and multiplied the third highest initial risk score.

* * * * *